(12) United States Patent
Otera

(10) Patent No.: US 10,485,448 B2
(45) Date of Patent: Nov. 26, 2019

(54) BREATH SENSOR, BREATH SENSOR UNIT, AND BREATH SENSING METHOD

(71) Applicant: Murata Manufacturing Co., Ltd., Nagaokakyo-shi, Kyoto-fu (JP)

(72) Inventor: Shozo Otera, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 127 days.

(21) Appl. No.: 15/696,663

(22) Filed: Sep. 6, 2017

(65) Prior Publication Data

US 2017/0360328 A1    Dec. 21, 2017

Related U.S. Application Data

(63) Continuation of application No. PCT/JP2015/081512, filed on Nov. 9, 2015.

(30) Foreign Application Priority Data

Apr. 15, 2015    (JP) .................................. 2015-083283

(51) Int. Cl.
    *A61B 5/08*       (2006.01)
    *G01N 27/333*     (2006.01)
    (Continued)

(52) U.S. Cl.
    CPC ............ *A61B 5/082* (2013.01); *A61B 5/0803* (2013.01); *A61B 5/0816* (2013.01);
    (Continued)

(58) Field of Classification Search
    CPC ............... G01N 27/416; G01N 33/497; G01N 27/3335; G01N 27/4074; A61B 5/742; A61B 5/7278; A61B 5/7246; A61B 5/0816; A61B 5/0803; A61B 5/082
    See application file for complete search history.

(56) References Cited

U.S. PATENT DOCUMENTS

| 7,608,047 B2 | 10/2009 | Stasz | |
| 2007/0012089 A1* | 1/2007 | Stasz | A61B 5/0878 73/31.01 |

(Continued)

FOREIGN PATENT DOCUMENTS

| CN | 101059466 A | 10/2007 |
| CN | 101186139 A | 5/2008 |

(Continued)

OTHER PUBLICATIONS

International Search Report issued in International Application PCT/JP2015/081512, dated Jan. 19, 2016.

(Continued)

*Primary Examiner* — Charles A Marmor, II
*Assistant Examiner* — Joshua Daryl D Lannu
(74) *Attorney, Agent, or Firm* — Arent Fox LLP

(57) ABSTRACT

A breath sensor includes a base body, a first electrode provided on a part of a surface of the base body, a second electrode provided on a part of the surface of the base body, and a covering layer made of a material that does not pass moisture therethrough, the covering layer covering the second electrode with the base body. The base body is preferably made of a material whose surface potential changes due to attachment of moisture to one of a surface of the first electrode and the surface of the base body. A surface potential on a side of the first electrode of the base body changes when a breath containing moisture touches the surface of the first electrode.

17 Claims, 15 Drawing Sheets

(51) Int. Cl.
*A61B 5/00* (2006.01)
*G01N 27/416* (2006.01)
*G01N 27/407* (2006.01)
*G01N 33/497* (2006.01)

(52) U.S. Cl.
CPC .......... *A61B 5/7246* (2013.01); *A61B 5/7278* (2013.01); *A61B 5/742* (2013.01); *G01N 27/3335* (2013.01); *G01N 27/4074* (2013.01); *G01N 27/416* (2013.01); *G01N 33/497* (2013.01)

(56) References Cited

U.S. PATENT DOCUMENTS

| | | |
|---|---|---|
| 2008/0107803 A1 | 5/2008 | Kwon |
| 2008/0262370 A1 | 10/2008 | Varney et al. |
| 2010/0010362 A1 | 1/2010 | Stasz |

FOREIGN PATENT DOCUMENTS

| | | |
|---|---|---|
| JP | H03-286741 A | 12/1991 |
| JP | H09-262224 A | 10/1997 |
| JP | 2001242131 A | 9/2001 |
| JP | 2011-516190 A | 5/2011 |
| JP | 4989932 B2 | 8/2012 |
| WO | 2008122806 A1 | 10/2008 |

OTHER PUBLICATIONS

Written Opinion of the International Searching Authority issued in International Application PCT/JP2015/081512, dated Jan. 19, 2016.

\* cited by examiner

BREATH SENSOR, BREATH SENSOR UNIT, AND BREATH SENSING METHOD

CROSS REFERENCE TO RELATED APPLICATIONS

The present application is a continuation of International application No. PCT/JP2015/081512, filed on Nov. 9, 2015, which claims priority to Japanese Patent Applications Nos. 2015-083283, filed on Apr. 15, 2015, the entire contents of each of which are incorporated herein by reference.

TECHNICAL FIELD

The present invention relates to a breath sensor, a breath sensor unit, and a breath sensing method.

BACKGROUND ART

In some situations such as in clinical practice, sensors for monitoring a respiratory status of a patient are required.

Therefore, there is proposed a sensor including a polyvinylidene difluoride (PVDF) film having conductor layers on both sides, and electrodes provided on the both sides of the PVDF film (e.g., Japanese Patent No. 4989932). A sensor of this type evaluates presence or absence of breath based on a temperature change of the PVDF film due to a breath blown against the PVDF film.

SUMMARY OF THE INVENTION

Problem to be Solved by the Invention

However, the sensor described in the foregoing patent is susceptible to an external temperature environment or the like, as it detects presence or absence of breath based on temperature. Therefore, depending on the usage environment, this sensor may not be able to accurately evaluate presence or absence of breath.

The present invention is made in view of the above problem, and it is an object is to provide a breath sensor capable of accurately evaluating presence or absence of breath.

Means for Solving the Problem

In accordance with embodiments of the invention, a breath sensor comprises:
a base body having an outer surface;
a first electrode provided on part of the outer surface of the base body;
a second electrode provided on a part of the outer surface of the base body; and
a covering layer made of a material that does not pass moisture there through, the covering layer covering the second electrode,
the base body being made of a material whose surface potential changes due to attachment of moisture to the surface of the first electrode and/or the outer surface of the base body.

The base body of the breath sensor may have a film-like shape whose outer surface includes first and second opposed surfaces with the first electrode being provided on the first surface of the base body and the second electrode being provided on the second main surface of the base body.

In some embodiments, the base body has a film-like shape and the outer surface of the base body includes a main surface with the first and second electrodes being provided on the main surface of the base body. In some embodiments the main surface is planar.

The covering layer can comprise a cation exchange membrane.

The base body preferably comprises an anion exchange membrane but can also include a cation exchange membrane.

In some embodiments the cation and anion exchange members are both planar and lie one on top of the other with the anion exchange member being adjacent the first electrode and the cation exchange member being adjacent the second electrode.

In some embodiments the outer surface of the base body includes first and second surfaces and the first and second electrodes are located on the first and second surfaces, respectively. In some embodiments the first and second electrodes cover the entirety of the first and second surfaces.

In other embodiments, the outer surface of the base body includes a planar first surface and first and second electrodes are located on the first surface.

The invention is also directed to a breath sensor unit comprising:
the breath sensor according to claim 1;
a detector circuit configured to detect a potential difference between the first and second electrodes; and
a breath frequency calculation unit configured to calculate the number of breaths applied to the breath sensor during a predetermined period of time based on fluctuations of the potential difference.

The breath sensor unit can also include:
a memory for recording correlated information indicating the correlation between the potential difference and a moisture content; and
a moisture content calculation unit configured to calculate the moisture content in the breath based on the stored correlated information and the potential difference detected by the detector circuit.

The invention is also directed to a breath sensing method, comprising:
(a) detecting a potential difference between a first electrode and a second electrode of a breath sensor of the type that includes:
(1) a base body;
(2) the first and second electrodes being located on the base body; and
(3) a covering layer covering layer covering the second electrode and made of a material that does not pass moisture there through, the base body being made of a material whose surface potential changes due to attachment of moisture to a surface of the first electrode and/or a surface of the base body; and
calculating a number of breaths within a predetermined period of time based on fluctuation of the potential difference.

The breath sensing method can also calculate a moisture content in a single breath based on stored correlated information indicating the correlation between the potential difference during the single breath and the moisture content in the single breath.

DESCRIPTION OF PREFERRED EMBODIMENTS

Hereinafter, embodiments of the present invention will be described in detail with reference to the drawings.

Figure 1:
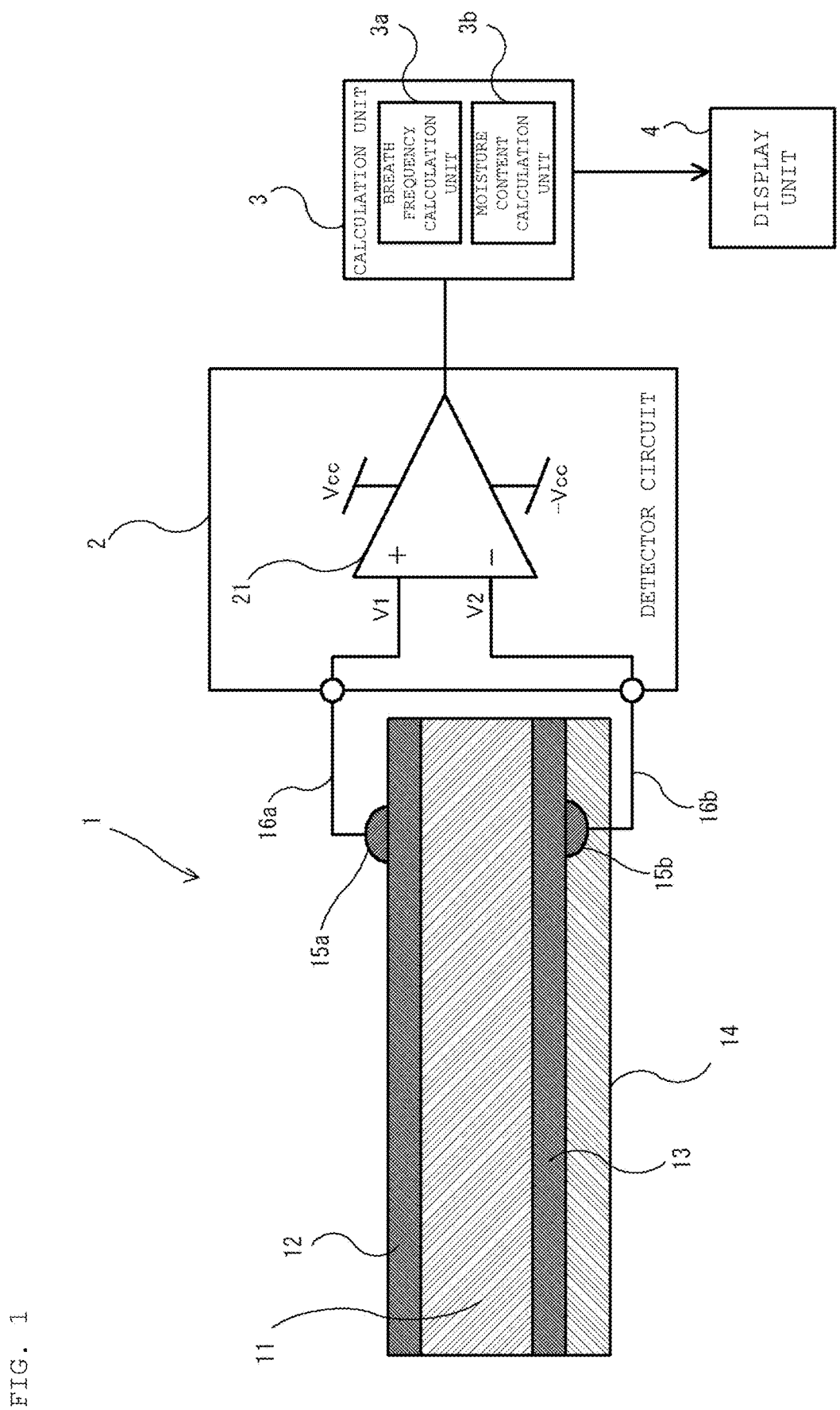
FIG. 1 is a configurational diagram of a breath sensor unit according to an embodiment.

A breath sensor unit according to the embodiment of FIG. 1 includes a breath sensor 1, a detector circuit 2 that detects a signal output from the breath sensor 1, a calculation unit 3 that calculates a number of breaths and a moisture content contained in the breath, and a display unit 4.

The breath sensor 1 includes a base body 11, a first electrode 12 provided on one main surface of the base body 11, a second electrode 13 provided on the other main surface of the base body 11, and a covering layer 14 that covers the lower surface of the second electrode 13 and thereby covers the lower surface of the base body 11 with the second electrode 13 therebetween. Lead wires 16a, 16b are connected to the first electrode 12 and the second electrode 13 via conductive members 15a, 15b.

When a breath is blown against the breath sensor 1 and moisture from the breath impinges on the first electrode 12 of the base body 11, hydrogen ions contained in the breath come into contact with the surface of the first electrode 12 causing the state of ions on the surface of the base body 11 to change. This, in turn, changes a surface potential of the base body 11. However, since no breath is blown against the second electrode 13 (because it is covered by the covering layer 14), the surface potential of the base body 11 at the lower surface thereof does not change. Therefore, the breath sensor 1 can be used to measure the frequency of a person's breath based on a fluctuation of a potential difference between the potential of the first and second electrodes 12 and 13.

Further, since the hydrogen ions are proportional to a moisture content in the breath, the potential difference between the potential of the first electrode 12 and the potential of the second electrode 13 will reflect the moisture content in the breath. Therefore, based on the potential difference between the potential of the first electrode 12 and the potential of the second electrode 13 of the breath sensor 1, it is possible to measure the moisture content in the breath.

In the following, preferred components of the breath sensor 1 will be described in detail. The base body 11 is preferably made of a cation exchange membrane whose surface potential on the side of the first electrode 12 of the base body 11 changes when a breath containing moisture is applied to the first electrode 12 or the base body 11. The base body 11 is preferably film-like, for example, in a 20 mm square shape in planar view. The cation exchange membrane is made, for example, of a perfluorocarbon material. Examples of such a cation exchange membrane include Nafion (registered trademark) available from Sigma-Aldrich and Selemion CMV (registered trademark) available from AGC Asahi Glass.

Because the base body 11 is made of a cation exchange membrane in this manner, it is possible to produce a potential difference which is sufficiently large to make it possible to detect a breath depending on its moisture content, between a portion to which moisture is attached and a portion other than this portion.

Figure 2A:
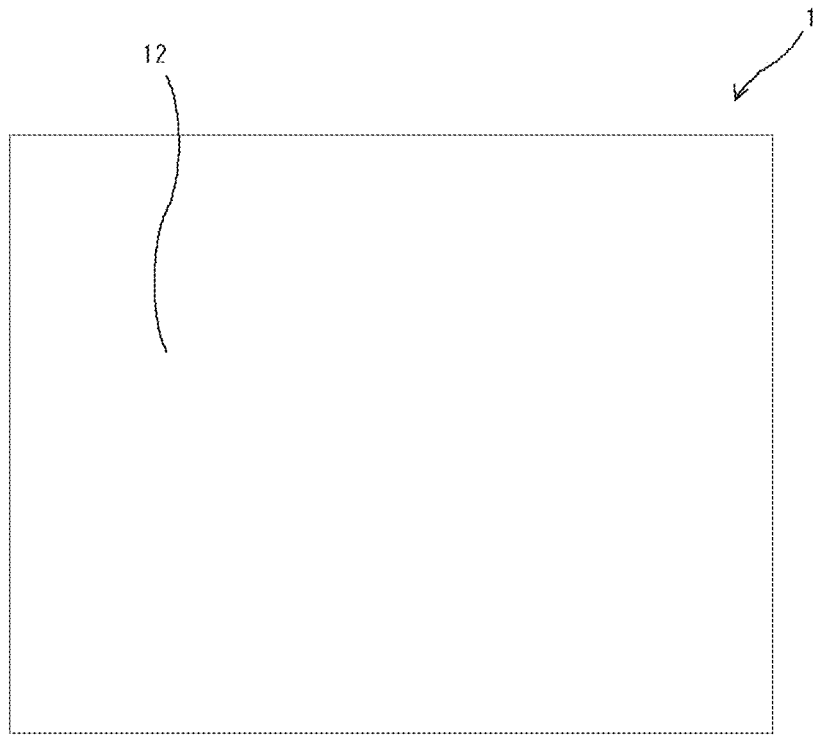
FIG. 2(A) is a plan view of a base body viewed from one main surface.

As shown in FIG. 2(A), the first electrode 12 is provided so as to preferably cover the entirety of one main surface of the base body 11. Further, the second electrode 13 is provided so as to preferably cover the entirety of the other main surface of the base body 11. The first and second electrodes 12 and 13 are preferably made of platinum (Pt) or the like and are preferably formed using a method such as sputtering, vapor-deposition, or plating.

Figure 2B:
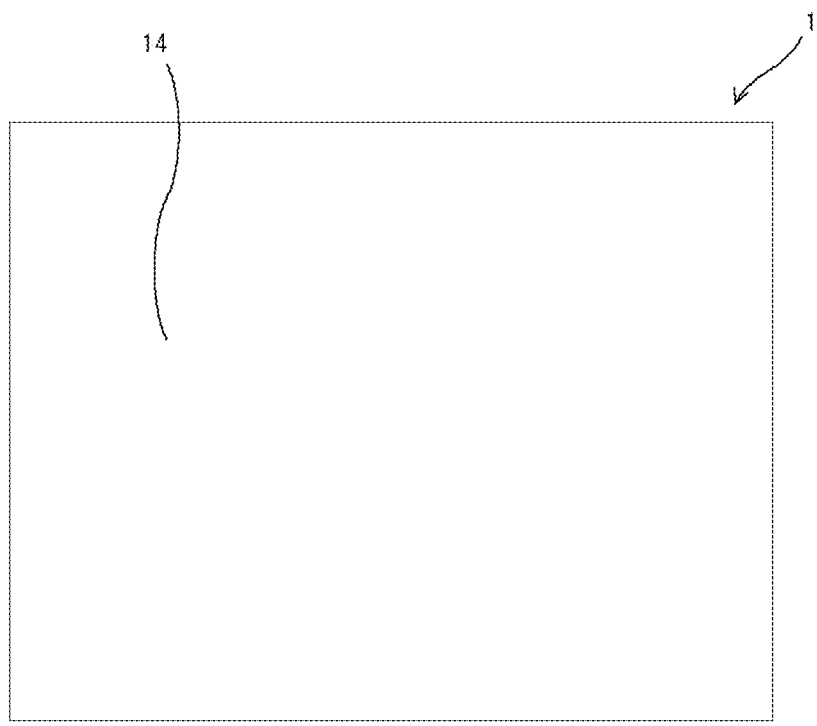
FIG. 2(B) is a plan view of the base body viewed from the other main surface.

The covering layer 14 is preferably made of a resin material or an anion exchange membrane that does not pass moisture therethrough, such as polyimide. As shown in FIG. 2(B), the covering layer 14 is preferably provided so as to entirely cover the second electrode 13 so as to entirely cover the bottom main surface of the base body 11 (as viewed in FIG. 1).

The conductive members 15a, 15b are preferably made of a conductive paste provided by mixing a metallic powder and a resin binder, for example. Examples of the conductive paste include "DOTITE FA-333 (registered trademark)"

available from Fujikura Kasei Co., Ltd. The lead wires 16a, 16b are preferably made of a metallic wire such as a copper wire.

The detector circuit 2 includes a differential amplifier circuit 21 that amplifies and outputs a potential difference between a positive input terminal and a negative input terminal. Constant voltages VCC, -VCC are supplied to the differential amplifier 21.

Figure 3:
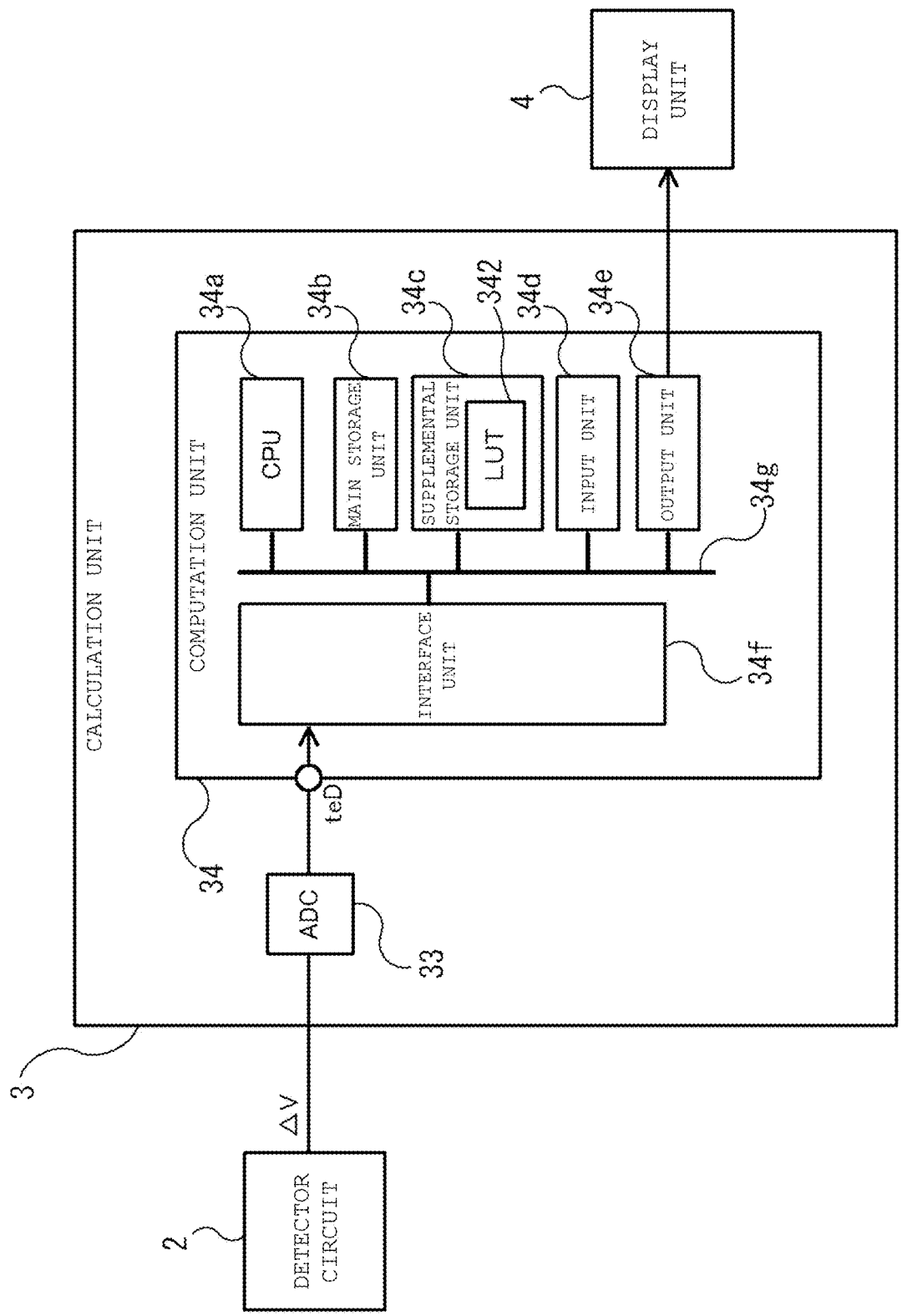
FIG. 3 is a configurational diagram of a calculation unit according to the embodiment.

The calculation unit 3 (FIG. 3) serves as both a breath frequency calculation unit 3a that calculates a frequency of breaths within a predetermined period of time and as a moisture content calculation unit 3b that calculates a moisture content in a single breath. As shown in FIG. 3, the calculation unit 3 as preferably a hardware configuration that includes an ADC (Analog to Digital converter) 33 and a computation unit 34. The computation unit 34 includes a CPU (Central Processing Unit) 34a, a main storage unit 34b, a supplemental storage unit 34c, an input unit 34d, an output unit 34e, an interface unit 34f, and a system bus 34g that connects these components. The computation unit 34 obtains a voltage value output from the ADC 33 as needed.

The CPU 34a reads and executes a program recorded in the supplemental storage unit 34c and controls the calculation unit 3 according to the program. The main storage unit 34b preferably includes a volatile memory such as a RAM (Random Access Memory). The main storage unit 34b is used as a workspace for the CPU 34a. The supplemental storage unit 34c preferably includes a non-volatile memory such as a magnetic disc, or a semiconductor memory. The supplemental storage unit 34c records the program executed by the CPU 34a and various parameters. Further, the supplemental storage unit 34c sequentially records results of processing by the CPU 34a and the like. Moreover, the supplemental storage unit 34c records a look-up table (LUT) 342 which provides an indication of the correlation between the potential difference between the first electrode 12 and the second electrode 13 and the moisture content in the breath.

The input unit 34d is for inputting information to the calculation unit 3 and is preferably configured by a touch panel or the like. The output unit 34e is connected to the display unit 4 and outputs data and the like obtained from the main storage unit 34b or the supplemental storage unit 34c via the system bus 34g to the display unit 4.

The display unit 4 is preferably a display which displays the frequency of breaths or the moisture content input from the calculation unit 3.

The ADC 33 continuously outputs a digital voltage value, obtained by sampling the voltage output from the detector circuit 2, to the computation unit 34. A sampling frequency of the ADC 33 is, for example, set to 100 kHz.

Next, an operation of the breath sensor unit according to this embodiment will be described. When the breath sensor 1 is positioned close to a patient's mouth, the breath sensor unit detects the frequency of breaths and the moisture content in each breath based on the fluctuation of the potential difference between the first and second electrodes 12 and 13 of the breath sensor 1. The breath sensor unit starts detection of the frequency of breaths and the moisture content in the breath of the patient upon accepting an operation by a user for starting detection of the frequency of breaths and the moisture content in the breath of the patient.

Figure 4:
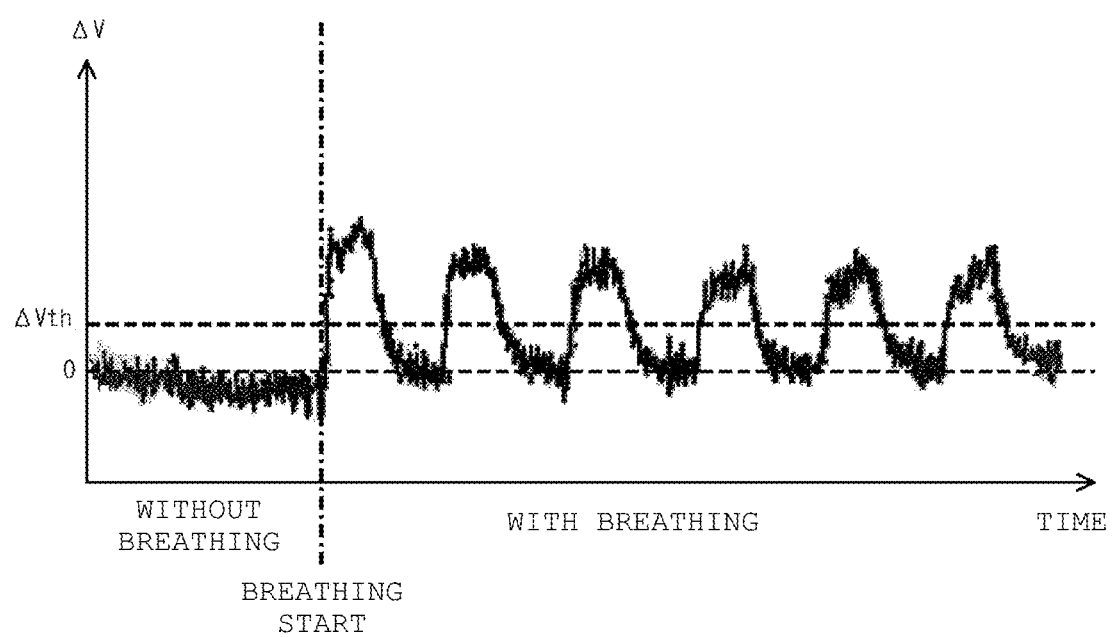
FIG. 4 is a diagram showing one example of an output signal of the breath sensor unit according to the embodiment.

FIG. 4 shows one example of a temporal waveform of a signal output from the detector circuit 2 of the breath sensor unit. As described above, the detector circuit 2 amplifies and outputs the potential difference between the first electrode 12 and the second electrode 13 of the breath sensor 1. When no breath is blown against the breath sensor 1, as indicated by a period labelled "without breathing" in FIG. 4, a temporal waveform of a voltage $\Delta V$ output from the detector circuit 2 hovers around 0 V. Then, when the patient starts blowing a breath against the breath sensor 1 at substantially regular intervals, as indicated by a period labelled "with breathing" in FIG. 4, the temporal waveform of the voltage $\Delta V$ output from the detector circuit 2 takes a waveform that changes according to the patient's breathing. Specifically, the temporal waveform of the voltage $\Delta V$ takes a waveform that exceeds a specific voltage threshold $\Delta V th$ substantially at regular intervals. In an example, the voltage $\Delta V$ in the state in which the breath is blown against the breath sensor 1 is approximately from 50 mV to 200 mV. The breath sensor unit detects the frequency of breaths of the patient and the moisture content in the breath from the fluctuation of the voltage $\Delta V$.

Figure 5:
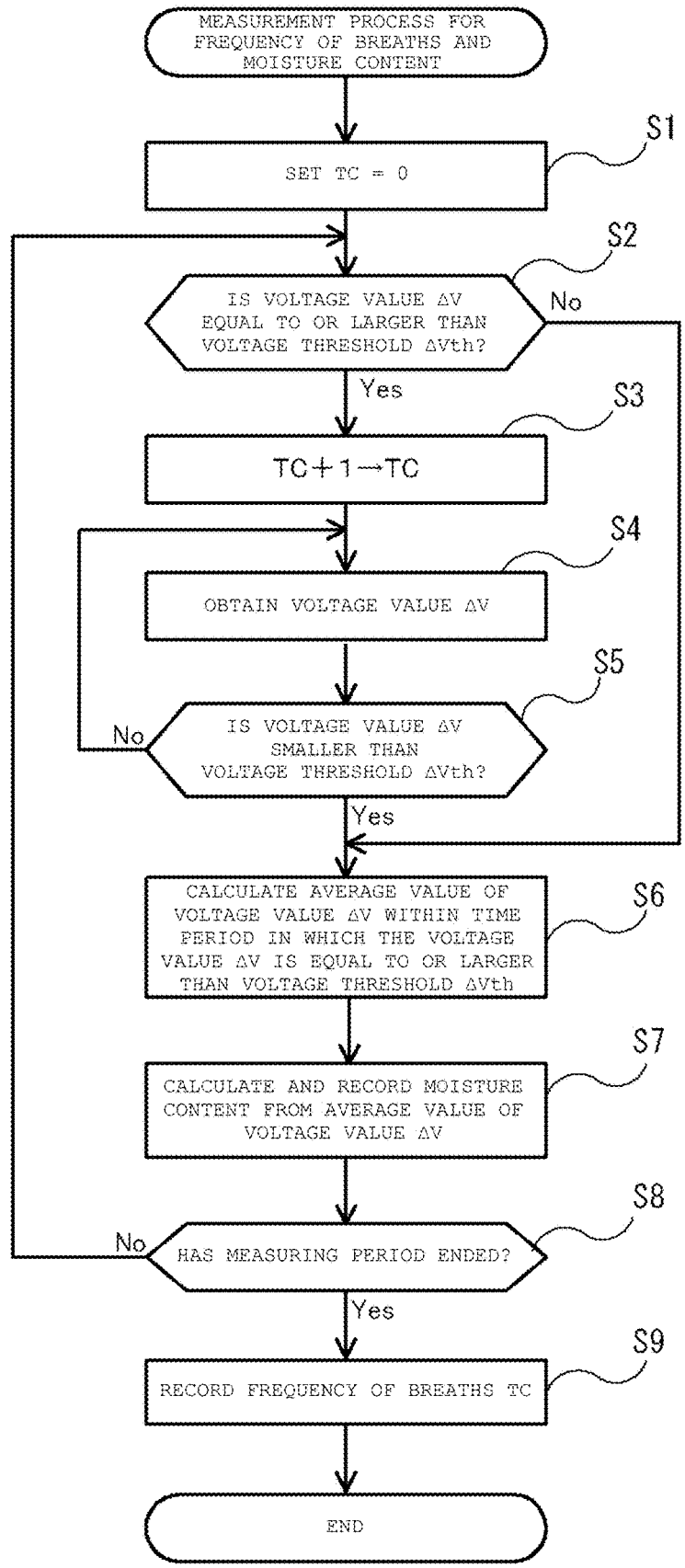
FIG. 5 is a flowchart showing one example of a measurement process for a number of breaths and a moisture content executed by the calculation unit according to the embodiment.

Next, a measurement process for the frequency of breaths and the moisture content executed by the breath sensor unit according to this embodiment will be described with reference to FIG. 5. The CPU 34a is preferably programmed to carry out the algorithm of FIG. 5. In this embodiment, the breath sensor unit calculates the number of times at which a voltage output from the detector circuit 2 transitions from a value smaller than a predetermined voltage threshold to a value equal to or greater than the predetermined voltage threshold within a given predetermined period of time (hereinafter the preset measuring period) and determines the frequency of breaths to be equal to the calculated number. Further, the breath sensor unit calculates the moisture content in the breath for a single breath based on an average voltage value during a period in which the voltage output from the detector circuit 2 hovers around a value equal to or larger than the voltage threshold.

First, the computation unit 34 sets a counting value TC of a breath counter to "0" (Step S1). Next, the computation unit 34 determines whether the voltage value $\Delta V$ input from the ADC 33 is equal to or larger than a previously set voltage threshold (Step S2). If the computation unit 34 has determined that the voltage value is smaller than the voltage threshold (Step S2: No), an operation in Step S6 is directly executed. On the other hand, if the voltage value $\Delta V$ is determined to be equal to or larger than the voltage threshold $\Delta V th$ (Step S2: Yes), the computation unit 34 increments the counting value TC by "1" (Step S3).

Next, the computation unit 34 obtains the voltage value $\Delta V$ input from the ADC 33 and records the obtained value in the main storage unit 34b (Step S4). Thereafter, the computation unit 34 determines whether the voltage value $\Delta V$ input from the ADC 33 is smaller than the voltage threshold $\Delta V th$ (Step S5). As long as the voltage value $\Delta V$ is equal to or larger than the voltage threshold $\Delta V th$ (Step S5: No), the computation unit 34 repeatedly obtains the voltage value $\Delta V$ input from the ADC 33 and records the obtained value in the main storage unit 34b (Step S4). On the other hand, if the voltage value $\Delta V$ is determined to be smaller than the voltage threshold $\Delta V th$ (Step S5: Yes), the computation unit 34 calculates an average value of the voltage value $\Delta V$ by dividing an integrated value of the voltage value $\Delta V$ during a time period in which the voltage value $\Delta V$ hovers around a value equal to or larger than the voltage threshold $\Delta V th$ by a number of data pieces for the voltage value $\Delta V$ obtained in the same period, and records the calculated value in the supplemental storage unit 34c (Step S6). Here, the computation unit 34 calculates the integrated value of the voltage value $\Delta V$ by integrating the voltage value $\Delta V$ during the time period in which the voltage value $\Delta V$ hovers around a value equal to the voltage threshold ΔVth recorded in the main storage unit 34b. Then, the computation unit 34 calculates the number of data pieces for the voltage value ΔV recorded in the main storage unit 34b, and calculates the average value of the voltage value ΔV by division of the calculated integrated value by the number of data pieces.

Figure 6:
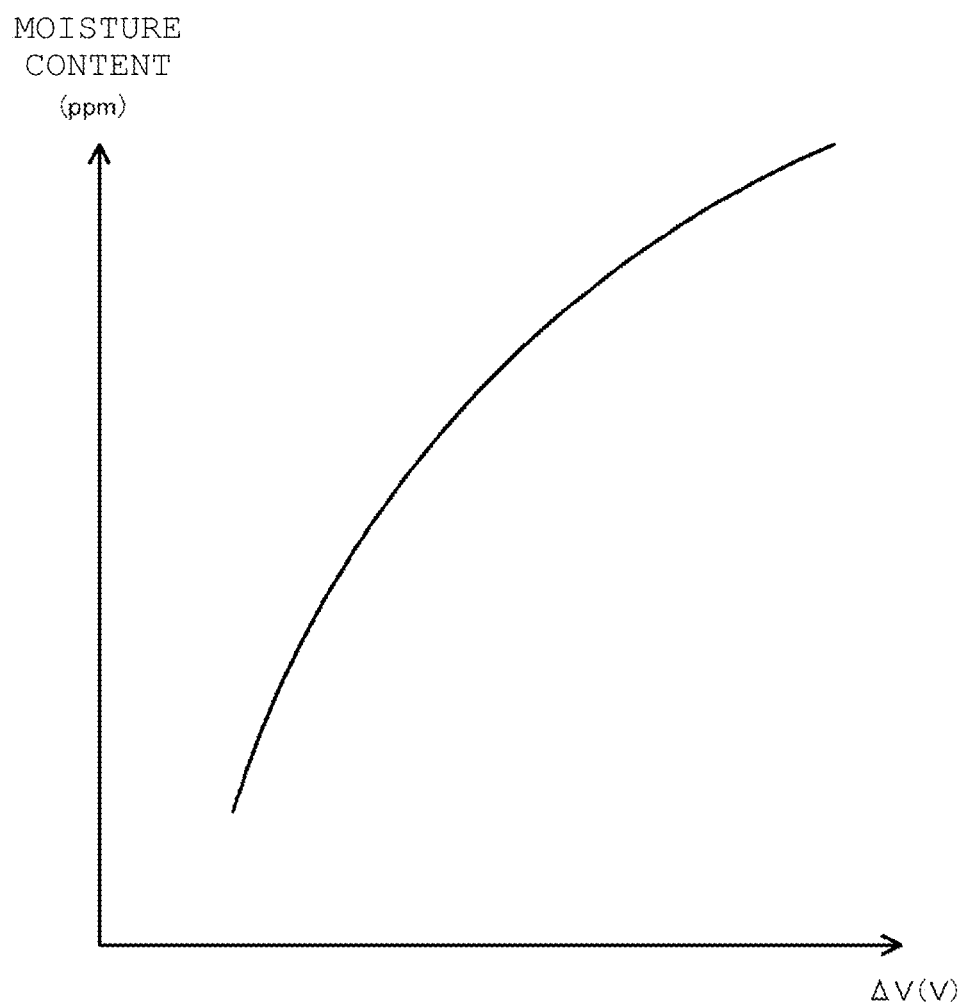
FIG. 6 is a diagram showing correlation between a voltage and the moisture content recorded in a look-up table according to the embodiment.

Thereafter, the computation unit 34 refers the look-up table 342 recorded in the supplemental storage unit 34c, calculates a moisture content based on the calculated average value of the voltage value ΔV, and records the calculated moisture content in the supplemental storage unit 34c (Step S7). The look-up table 342 shows correlation between the voltage value ΔV and the moisture content as shown in graphical form in FIG. 6, for example. The look-up table 342 can be determined by measuring humidity (moisture content) of a humidified gas to be blown against the breath sensor 1 and the voltage value ΔV while changing the humidity of the humidified gas.

Then, the computation unit 34 determines whether or not the measuring period has ended (Step S8), and if the preset measuring period has not ended (Step S8: No), the computation unit 34 again executes the operation in Step S2. Here, based on the counting value of the timer, the computation unit 34 determines whether or not the preset measuring period has ended. Until the preset measuring period ends, the computation unit 34 repeatedly performs the operations from Step S2 to Step S7. It should be noted that a repeating interval of the operations from Step S2 to Step S7 is selected to be sufficiently shorter than a time period for exhalation of a person in a single breath and an interval of breathing by a person.

On the other hand, if the preset measuring period has ended (Step S8: Yes), the computation unit 34 records a number set for the counting value TC as the frequency of breaths in the supplemental storage unit 34c (Step S9) and terminates the measurement process for the frequency of breaths and the moisture content. Then, the output unit 34e of the computation unit 34 outputs history of the moisture content of each breath and the frequency of breaths during the measuring period recorded in the supplemental storage unit 34c to the display unit 4.

As described above, according to the breath sensor 1 of this embodiment, it is possible to detect the presence or absence of a breath by detecting a potential difference between the surface of the base body 11 on the side of the first electrode 12 and the surface of the base body 11 on the side of the second electrode 13 produced when a breath containing moisture touches the surface of the first electrode 12. In other words, it is possible to detect the presence or absence of a breath based on presence or absence of moisture contained in the breath. The presence or absence of breath may be detected regardless of the temperature environment in which the breath sensor 1 is used. As a result, it is possible to more accurately detect the presence or absence of the patient's breath compared to the configuration for detecting presence or absence of breath based on temperature of the patient's breath.

Further, in the breath sensor 1 according to this embodiment, it is possible to have the first electrode 12 entirely cover one surface of the base body 11 and/or the second electrode 13 so as to entirely cover the other surface of the base body 11. In this case, when the first electrode 12 and the second electrode 13 are formed using sputtering or the like, it is possible to simplify the manufacturing method because the patterning of a conductor layer over the surface of the base body 11 is not necessary. Moreover, the computation unit 34 according to this embodiment calculates the frequency of breaths within the previously set measuring period based on fluctuation of the potential difference between the first electrode 12 and the second electrode 13. With this, it is possible to accurately measure the frequency of breaths within the measuring period regardless of the temperature environment.

Furthermore, the breath sensor unit according to this embodiment includes the detector circuit 2 that outputs a voltage proportional to the potential difference produced between a portion of the base body 11 that is covered by the covering layer 14 and a portion of the base body 11 that is not covered by the covering layer 14 when breath containing moisture is blown against the breath sensor 1. The potential difference produced between the portion of the base body 11 that is covered by the covering layer 14 and the portion of the base body 11 that is not covered by the covering layer 14 becomes larger as the moisture content contained in the patient's breath is higher. The computation unit 34 refers the look-up table 342 indicating the correlation between the voltage ΔV and the moisture content in the breath and calculates the moisture content in the breath for a single breath based on the voltage ΔV output from the detector circuit 2. With this, it is possible to evaluate the moisture content in the patient's breath.

In monitoring a respiratory status of a patient, it is also desired to monitor whether or not the moisture content of the patient's breath is normal, in order to detect an abnormity in a respiratory system of the patient. One such sensor employing a capacitor made of a polymer membrane has been proposed in Yutaka USUDA, "Heated Humidification and Airway Care; Problems of Heated Humidification for Artificial Airway", Artificial Respiration, Vol. 27, No. 1 (2010) pp. 57 to 63 (hereinafter "Usuda"). This sensor is to detect humidity in a breath utilizing the fact that moisture contained in the breath is absorbed into the polymer membrane of the capacitor and therefore the electrostatic capacitance of the capacitor changes when a breath is blown against the capacitor. However, the response time of the Usuda sensor is at best, from 2 seconds to 5 seconds. On the other hand, a time interval of a human breath impinging on the sensor is usually shorter than 1 second. Therefore, the sensor described in Usuda may not be able to evaluate the moisture content of a single breath.

In contrast, as described above, the breath sensor unit according to this embodiment is able to evaluate the moisture content in a single breath and therefore it is possible to monitor the respiratory status of the patient more strictly.

While a preferred embodiment of the present invention has been described above, the present invention is not limited to the configuration of this embodiment. For example, it is possible to employ a configuration in which the first and second electrodes cover only a part of the upper and lower surfaces of the base body, leaving part of those surfaces exposed.

Figure 7:
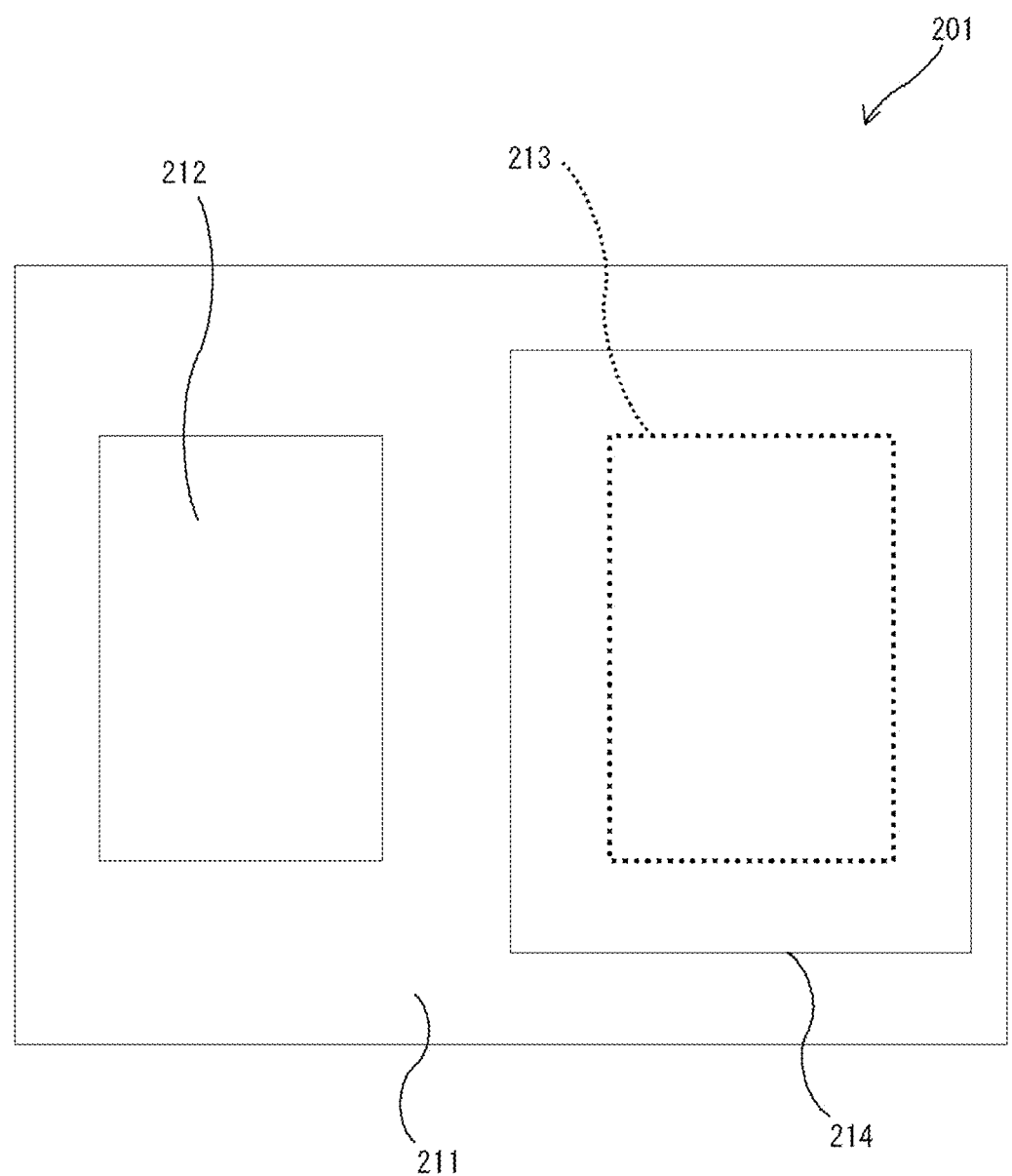
FIG. 7 is a plan view of a breath sensor according to a first variation of the embodiment.
Figure 8:
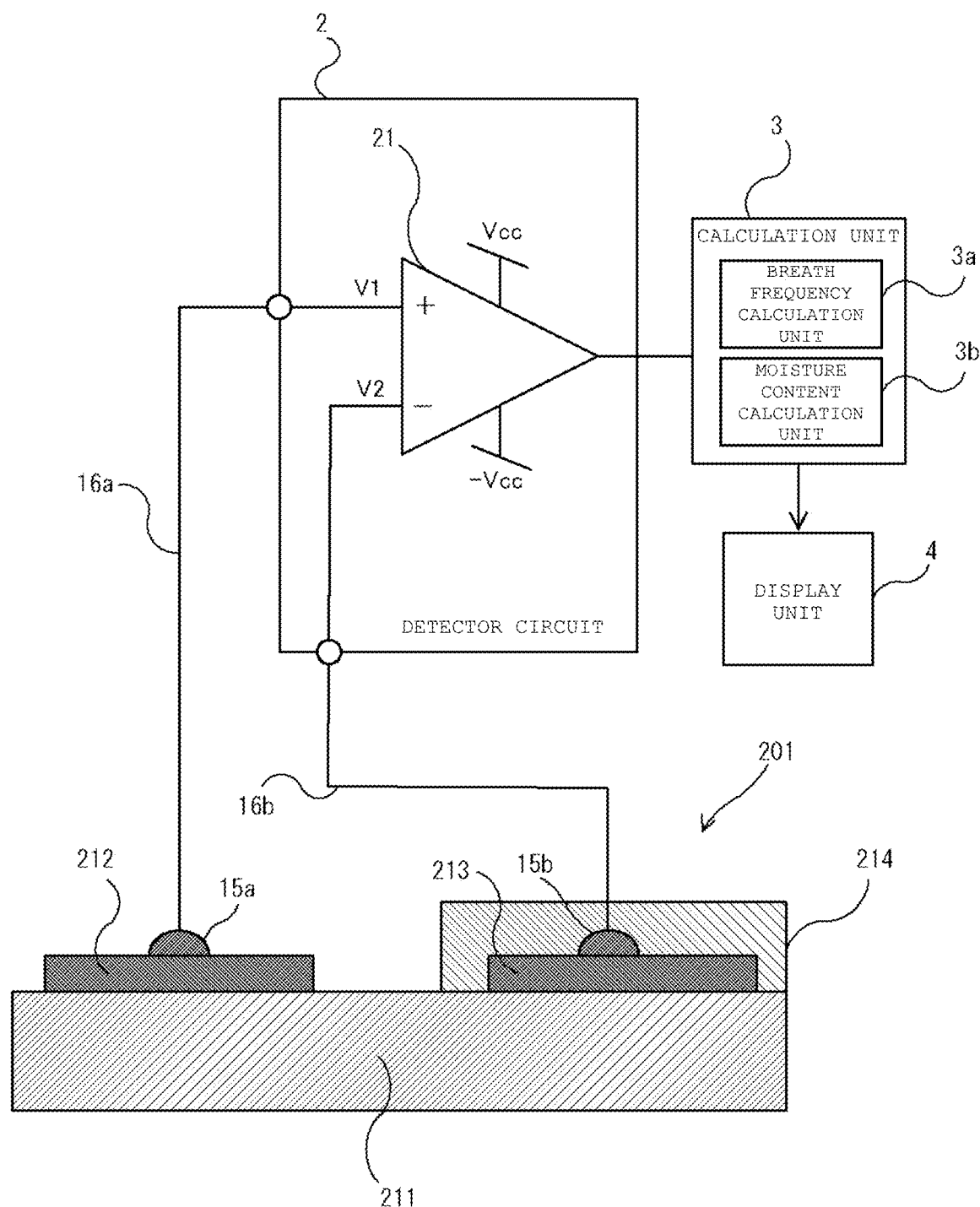
FIG. 8 is a configurational diagram of a breath sensor unit according to the first variation of the embodiment.

FIGS. 7 and 8 show one example in which a part of the surface of the base body is exposed. In this embodiment, the first and second electrodes 212 and 213 and the covering layer 214 are all formed on a single planar surface of the base body 211. However, a part of the surface of the base body 211 is exposed (i.e., is not covered by any of a first electrode 212, a second electrode 213 and a covering layer 214). In FIG. 8, like components as those in the embodiment are denoted by like reference numerals as in FIG. 1.

The base body 211 is preferably made of a cation exchange membrane and the first and second electrodes 212, 213 are preferably made of a metallic material. The covering layer 214 is preferably made of a resin material that does not pass moisture therethrough, such as polyimide.

According to this configuration, the first and second electrodes 212 and 213 are provided a single planar surface of the base body 211. With this configuration, the first and second electrodes 212 and 213 can be formed by sputtering or the like thereby reducing production costs because it is not necessary to turn the base body 211 over.

In the foregoing embodiments, the base body 11 is a single-layer structure, but the present invention is not so limited. For example, the base body may take a structure in which two or more layers made of e.g., cation exchange membranes are laminated together. Alternatively, the base body may take a configuration in which a layer made of a cation exchange membrane and a layer made of an anion exchange membrane whose surface potential does not change even when a breath containing moisture is applied to the surface of the electrode or the base body are laminated together. Other configurations are possible.

Figure 9:
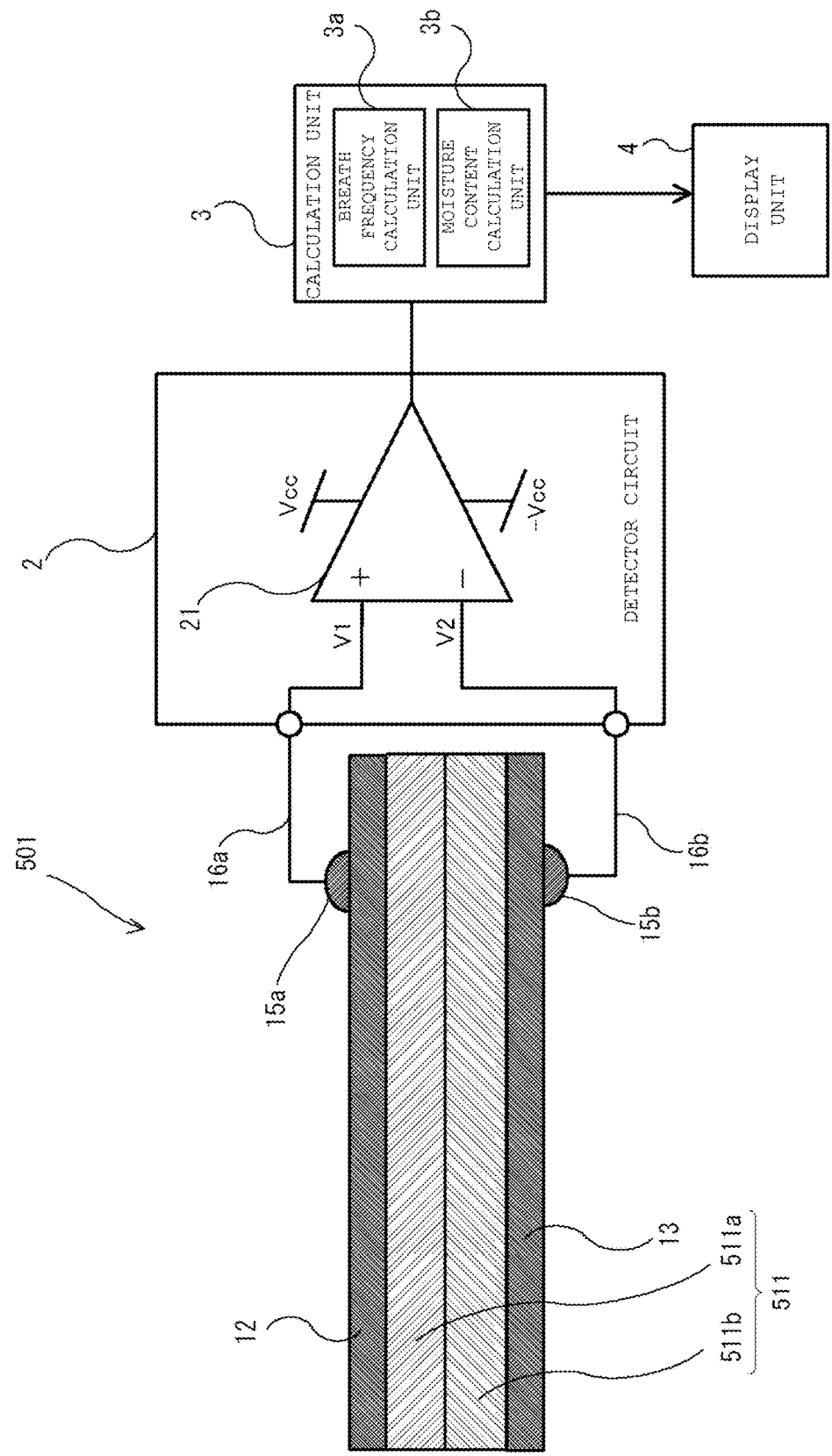
FIG. 9 is a configurational diagram of a breath sensor unit according to a second variation of the embodiment.

FIG. 9 shows a variation of a breath sensor having a configuration in which a layer made of a cation exchange membrane and a layer made of an anion exchange membrane are laminated together. The breath sensor 501 includes a base body 511 configured by a first sub base body 511a and a second sub base body 511b that are laminated together. The first sub base body 511a is made of a cation exchange membrane and the second sub base body 511b is made of a material such as an anion exchange membrane whose surface potential on a side of the second electrode 13 does not change even when a breath containing moisture touches the surface of the second electrode 13.

Figure 10:
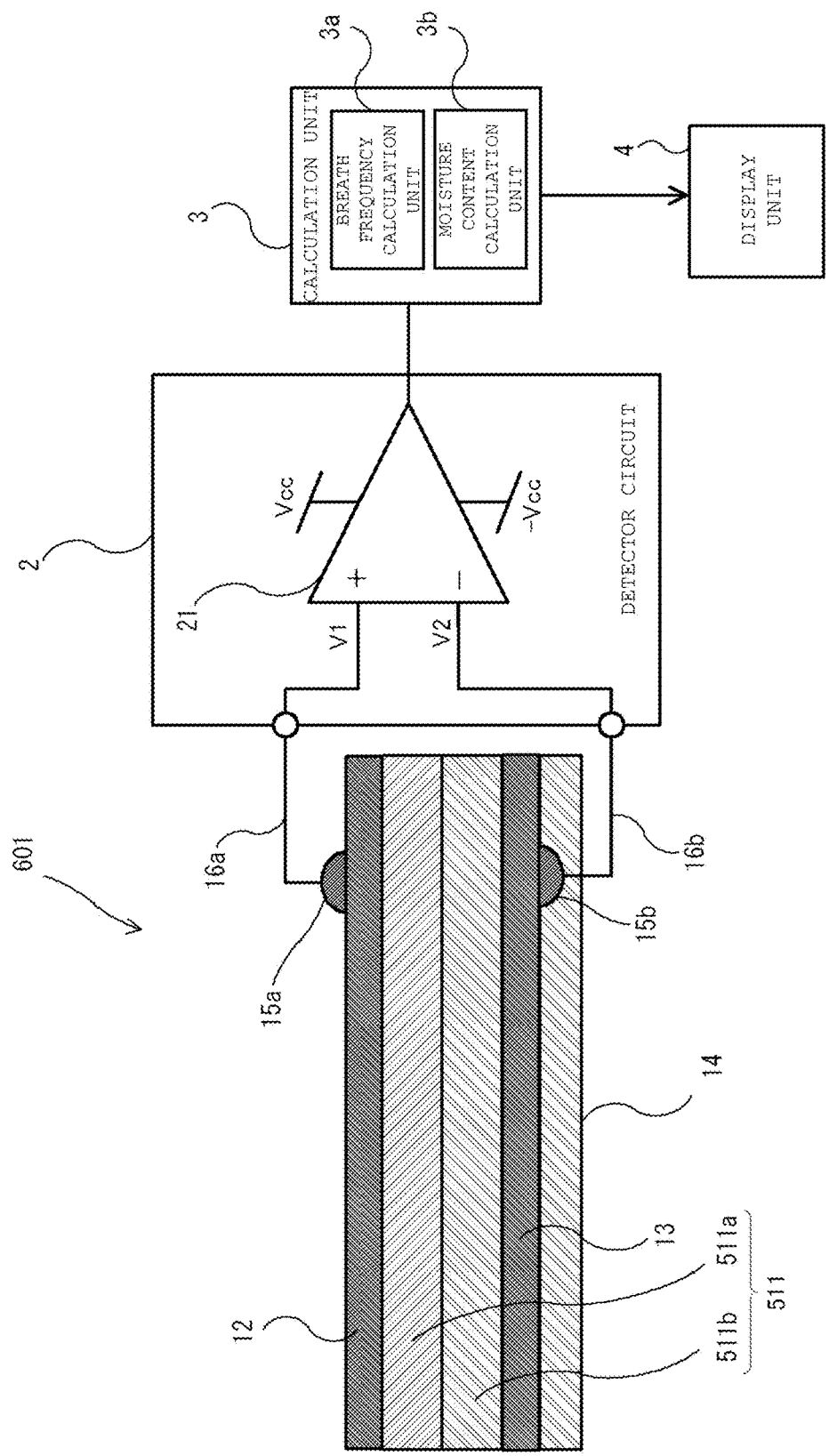
FIG. 10 is a configurational diagram of a breath sensor unit according to the second variation of the embodiment.

FIG. 10 shows another variation having a configuration in which a layer made of a cation exchange membrane and a layer made of a anion exchange membrane are laminated together. In FIG. 10, like components as those in the configuration shown in FIG. 9 are denoted by like reference numerals as in FIG. 9. In this embodiment, the breath sensor 601, the second sub base body 511b, which is preferably made of a material such as an anion exchange membrane, is disposed next to the second electrode 13 that is covered by the covering layer 14. Further, the first sub base body 511a, preferably made of a cation exchange membrane, is disposed next to the first electrode 12 that is not covered by the covering layer.

According to this configuration, a difference between a surface potential of the base body 511 on the side of the second electrode 13 and a surface potential of the base body 511 on the side of the first electrode 12 becomes noticeable. Therefore, it is possible to measure the presence or absence of a breath, and a moisture content of each breath, with a high accuracy compared to a configuration in which the base body has a single-layer structure made of a cation exchange membrane (for example, the breath sensor 1 according to the embodiment of FIG. 1).

In the above described embodiments the base body 11 is film-like. However, the shape of the base body 11 is not limited to such an example, and may have a different shape such as a plate shape or a cuboid. In a case in which the base body is a cuboid, for example, the electrodes may be provided on perpendicular surfaces.

The configuration in which the breath sensor unit according to the embodiment measures both the frequency of breaths within the previously set measuring period and the moisture content of each breath has been described. However, the present invention is not limited to such an example and may, for example, provide a configuration that only measures the frequency of breaths.

Figure 11:
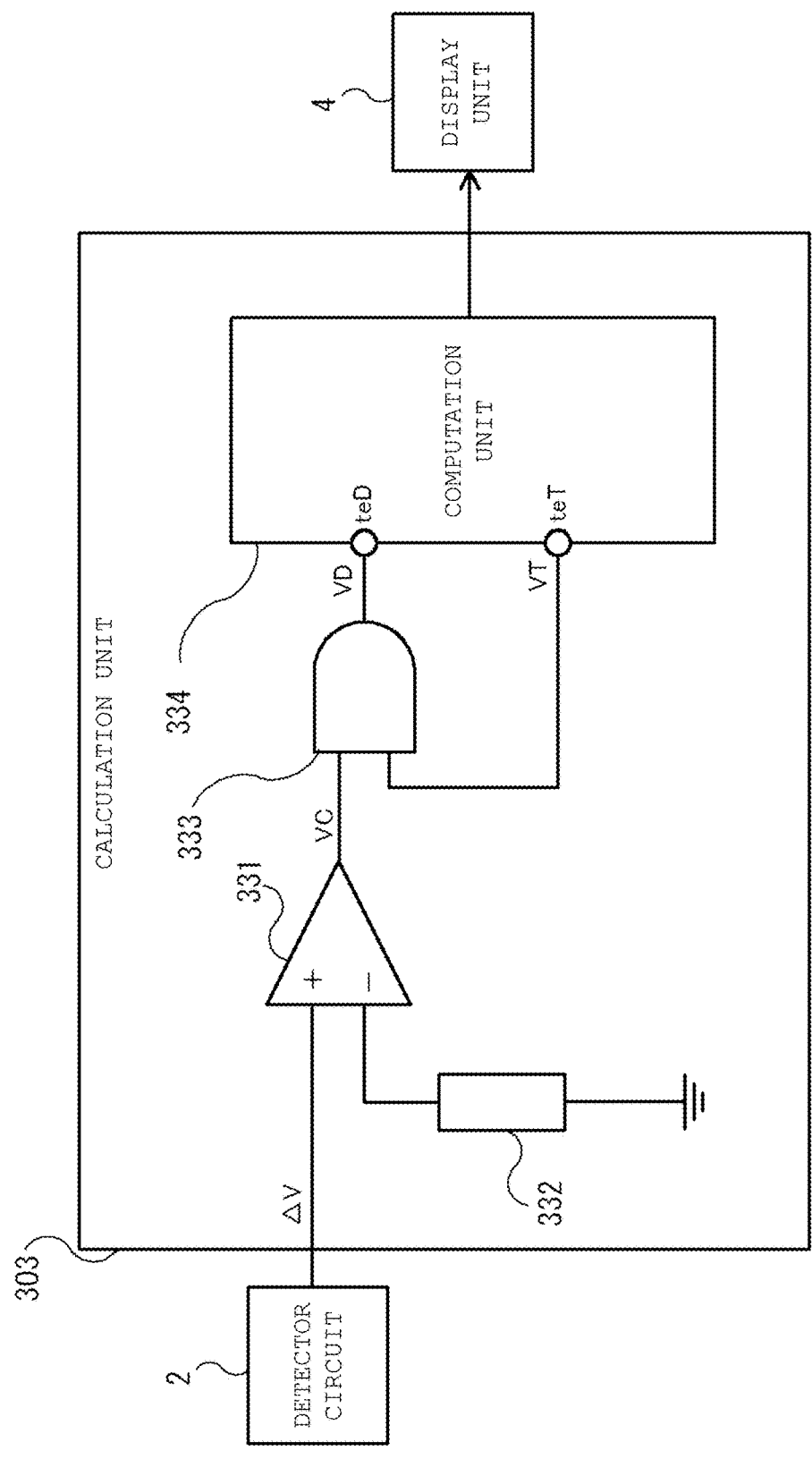
FIG. 11 is a configurational diagram of a calculation unit according to a third variation of the embodiment.

FIG. 11 shows a breath sensor unit that only measures the frequency of the patient's breaths. This breath sensor unit includes a comparator 331, a reference voltage source 332, an AND circuit 333 and a computation unit 334. The comparator 331 preferably is configured by an operational amplifier or the like. A voltage signal from the detector circuit 2 is input to a positive input terminal and a reference voltage output from the reference voltage source 332 is input to a negative input terminal. If a voltage value of the voltage signal input from the detector circuit 2 is larger than an output voltage of the reference voltage source 332, the comparator 331 outputs a "High" level voltage. On the other hand, if the voltage value of the voltage signal input from the detector circuit 2 is smaller than the output voltage of the reference voltage source 332, the comparator 331 outputs a "Low" level voltage.

One input terminal of the AND circuit 333 is connected to an output terminal of the comparator 331 and the other input terminal of the AND circuit 333 is connected to a trigger terminal teT of the computation unit 334. Its output end is connected to a detector terminal teD of the computation unit 334. The AND circuit 333 outputs a voltage at different levels depending on the detected presence or absence of the patient's breath within the previously set period to the detector terminal teD of the computation unit 334.

The computation unit 334 has a similar configuration to the computation unit 34 shown in FIG. 3 but includes the trigger output terminal teT. Like components as those in the configuration shown in this embodiment are described using like reference numerals to those used in FIG. 3.

In the present embodiment, CPU 34a (FIG. 3) controls a voltage at the trigger terminal teT via the interface unit 34f. The computation unit 334 maintains the voltage of the trigger terminal teT at the "High" level during the preset measuring period and maintains the voltage of the trigger terminal teT at the "Low" level at other times. Further, the computation unit 334 increments the counting value by 1 when the voltage of the detector terminal teD is switched from the "Low" level to the "High" level. Further, the computation unit 334 records the counting value of the breath counter in the supplemental storage unit 34c when the voltage of the trigger terminal teT is switched from the "High" level to the "Low" level.

Figure 12:
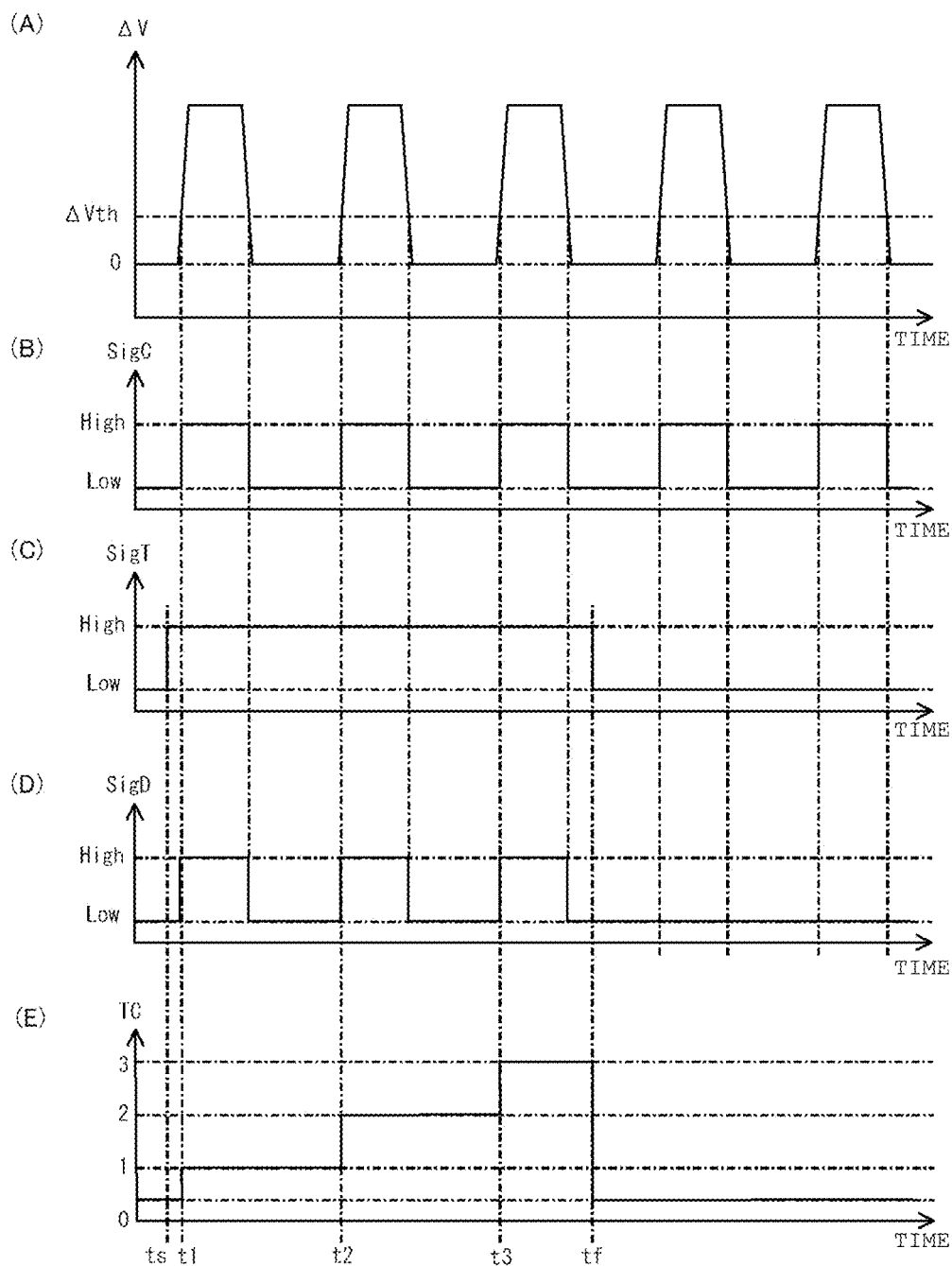
FIG. 12 is a timing chart showing one example of relation, according to the third variation of the embodiment, between an output voltage of a detector circuit, an output voltage of a comparator, a voltage of a trigger terminal of a computation unit, an input voltage to a detector terminal of the computation unit, and a counting value of a breath counter, wherein (A) is a timing chart of the output voltage of the detector circuit, (B) is a timing chart of the output voltage of the comparator, (C) is a timing chart of the voltage of the trigger terminal of the computation unit, (D) is a timing chart of the input voltage to the detector terminal of the computation unit, and (E) is a timing chart of the counting value of the breath counter.

In FIG. 12, graphs (A) to (C) are time charts showing one example of the relation between the output the voltage ΔV of the detector circuit 2, the output voltage VC of the comparator 331, a voltage VT of the trigger terminal teT of the computation unit 334, an input voltage VD to the detector terminal teD of the computation unit 334 in the present embodiment. Here, the output voltage of the reference voltage source 332 is equal to the voltage threshold ΔVth. The input voltage VD to the detector terminal teD shows a voltage waveform in a rectangular waveform according to a waveform of the voltage ΔV only during a time period from time is (at which the voltage of the trigger terminal teT is at the "High" level) to time tf. The computation unit 334 increments the counting value of the breath counter by "1" each time the voltage of the detector terminal teD is switched from the "Low" to the "High" level (i.e., at time instances t1, t2, and t3). Then, at time tf, the computation unit 334 records the counting value "3" of the breath counter in the supplemental storage unit 34c and resets the counting value of the breath counter to "0". According to this configuration, it is possible to simplify the process executed by the computation unit 334 and therefore to reduce loads on the computation unit 334.

The configuration of the breath sensor unit according to an embodiment in which the calculation unit 3 measures both the frequency of breaths within the previously set measuring period and the moisture content in each breath by processing in a software manner data obtained by sampling a voltage signal output from the detector circuit 2 is now described with reference to FIGS. 13-15. However, the present invention is not limited to such an example. For example, a configuration in which hardware components such as an integration circuit and a differentiation circuit are combined may be used.

Figure 13:
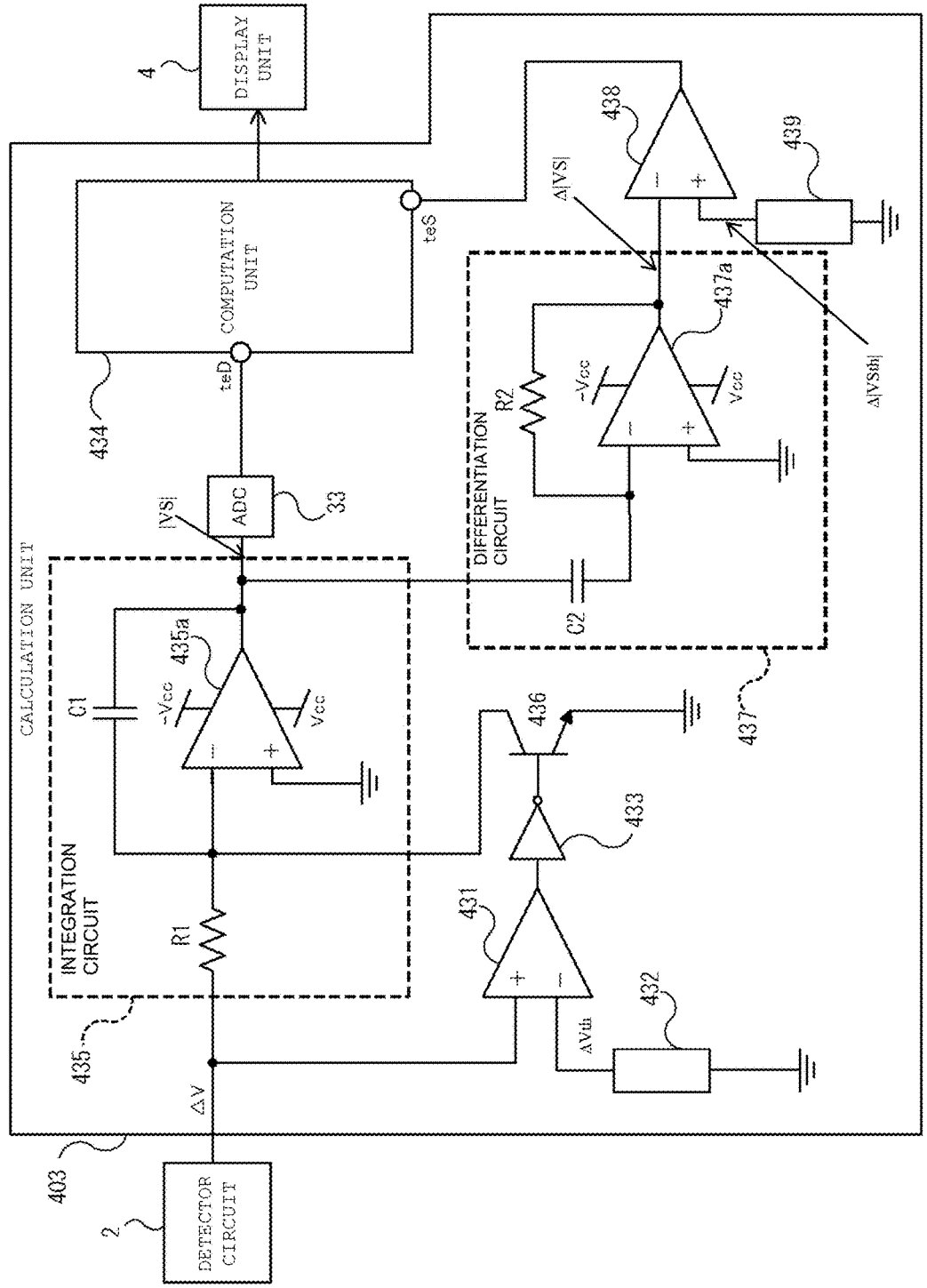
FIG. 13 is a configurational diagram of a calculation unit according to a fourth variation of the embodiment.

In the embodiment of FIG. 13, a breath sensor unit includes comparators 431, 438, reference voltage sources 432, 439, an inverter 433, an integration circuit 435, a transistor 436, a differentiation circuit 437, the ADC 33, and a computation unit 434. In FIG. 13, like components as those in the previously described embodiment are denoted by like reference numerals as in the embodiment. Like the configuration shown in FIG. 11, the comparator 431 is preferably configured such that a voltage signal from the detector circuit 2 is input to a positive input terminal and a reference voltage output from the reference voltage source 432 is input to a negative input terminal of the comparator 431. The inverter 433 is preferably configured by an inverting amplifier or the like, and outputs a "Low" level voltage if an output voltage of the comparator 431 is at the "High" level, and outputs a "High" level voltage if the output voltage of the comparator 431 is at the "Low" level. The integration circuit 435 is preferably configured by an operational amplifier 435a, a resistor R1, and a capacitor C1. The switching element 436 is preferably configured by an NPN transistor and has a collector connected to a negative input terminal of the operational amplifier 435a of the integration circuit 435, an emitter that is grounded and a base connected to an output terminal of the inverter 433. The switching element 436 is switched to an on state if the voltage $\Delta V$ output from the detector circuit 2 is lower than the reference voltage. At this time, an input to the negative input terminal of the operational amplifier 435a is forcibly set to a zero level. The differentiation circuit 437 is preferably configured by an operational amplifier 437a, a resistor R2, and a capacitor C2. The comparator 438 is preferably configured such that a reference voltage output from the reference voltage source 439 is input to a positive input terminal and a voltage signal output from the differentiation circuit 437 is input to a negative input terminal. If a voltage input from the differentiation circuit 437 is lower than the reference voltage, the comparator 438 outputs a "High" level voltage to a falling detector terminal teS of the computation unit 434.

The computation unit 434 has substantially the same structure as the computation unit 3 of the embodiment of FIG. 3 but includes a falling detector input terminal teS for detecting a reduction of the absolute value |VS| of the output voltage of the integration circuit 435 as described further below. Here, like components as those in the embodiment are described using like reference numerals to those used in FIG. 3. In this embodiment, the CPU 34a (FIG. 3) detects a voltage at the falling detector terminal teS via the interface unit 34f. Further, the computation unit 334 increments the counting value of the breath counter by "1" when a voltage at the falling detector terminal teD is switched from the "Low" level to the "High" level and calculates the moisture content based on an output voltage VS of the integration circuit 435.

Figure 14:
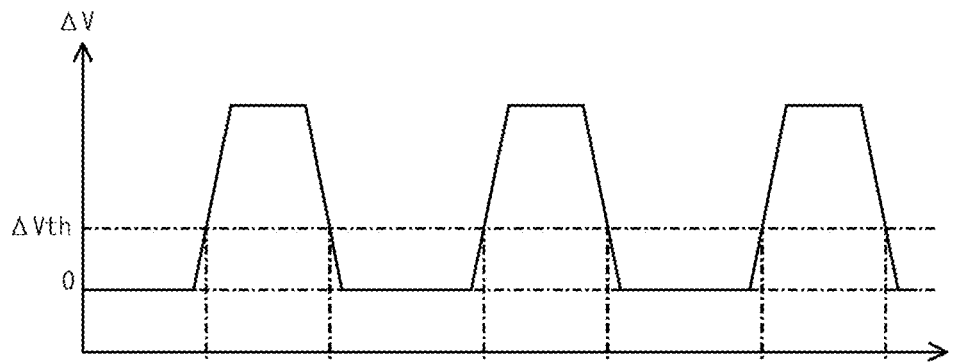
FIG. 14 is a timing chart showing one example of relation, according to the fourth variation of the embodiment, between an output voltage of a detector circuit, an absolute value of an output voltage of an integration circuit, and an output voltage of a differentiation circuit, wherein (A) is a timing chart of the output voltage of the detector circuit, (B) is a timing chart of the absolute value of the output voltage of the integration circuit, and (C) is a timing chart of the output voltage of the differentiation circuit.
Figure 14:
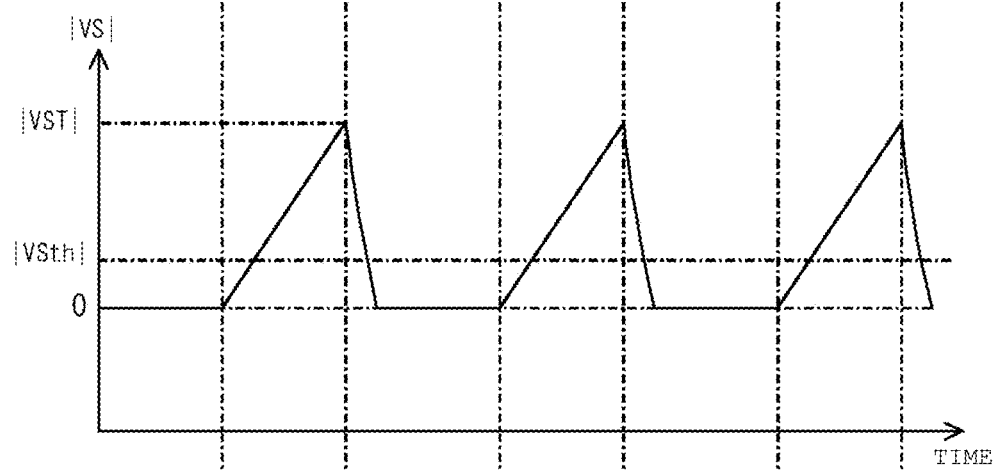
Figure 14:
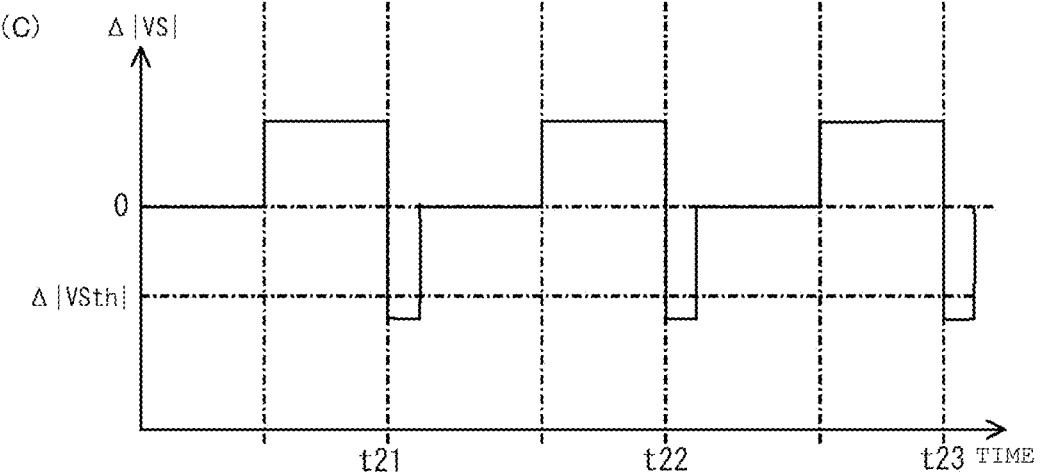
Figure 15:
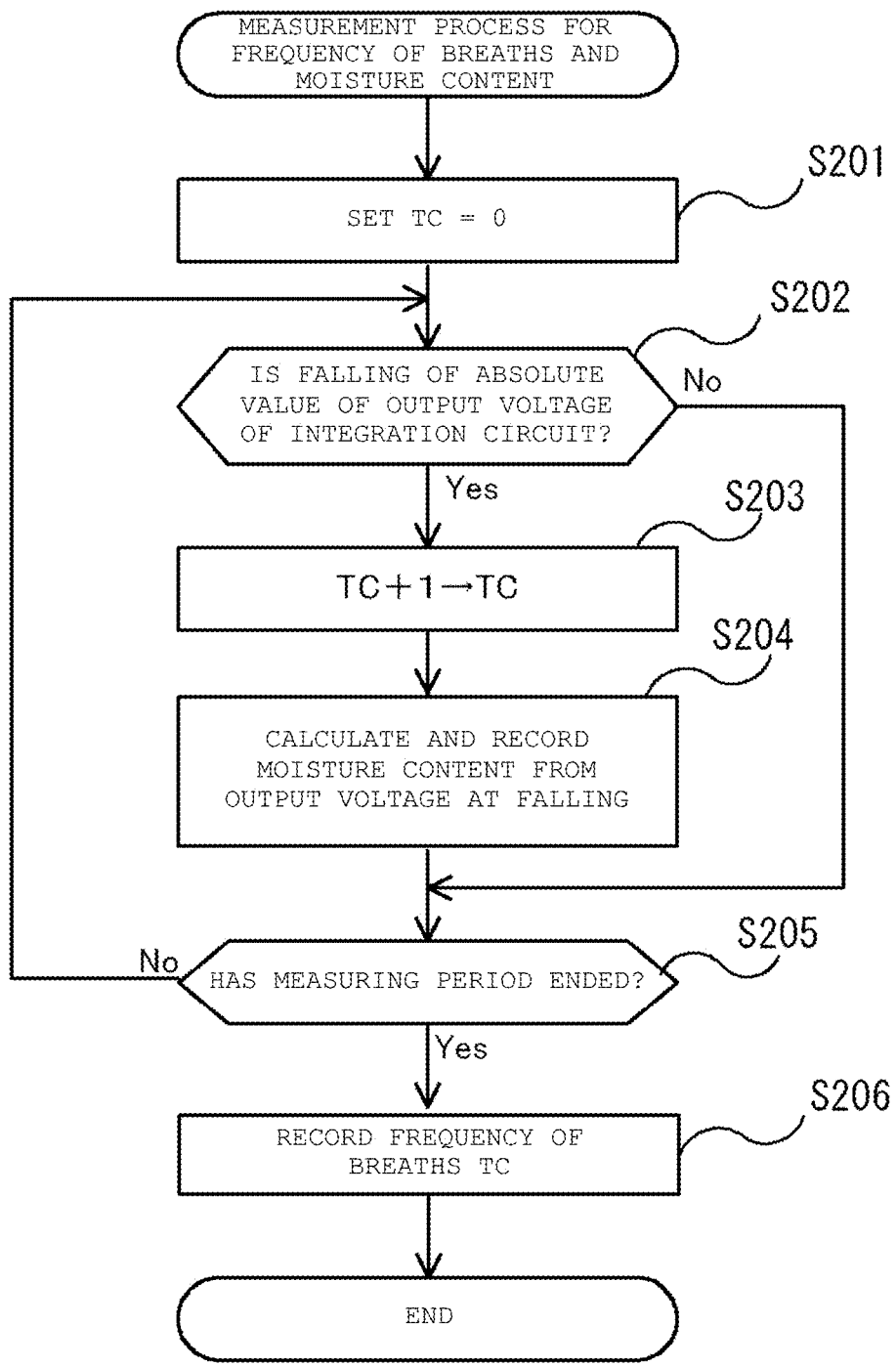
FIG. 15 is a flowchart showing one example of a measurement process for a number of breaths and a moisture content executed by the calculation unit according to the fourth variation of the embodiment.

In FIG. 14, graphs (A) to (C) are time charts showing one example of the relation between the output the voltage $\Delta V$ of the detector circuit 2, the absolute value |VS| of the output voltage VC of the integration circuit 435 and an output voltage $\Delta$|VS| of the differentiation circuit 437, respectively. Here, the output voltage of the reference voltage source 432 is equal to the voltage threshold $\Delta V$th. During the period when the voltage $\Delta V$ is smaller than the voltage threshold $\Delta V$th, the output voltage of the comparator 431 is at the "Low" level, the output voltage of the inverter 433 is at the "High" level and the transistor 436 is maintained in the on state. While transistor 436 is in the on state, the negative input terminal of the operational amplifier 435a is maintained at a ground potential, the absolute value |VS| of the output voltage of the integration circuit 435 is maintained at 0 V and the differential output $\Delta$|VS| of the differentiation circuit 437 is also zero. On the other hand, during the period when the voltage $\Delta V$ is equal to or greater than the voltage threshold $\Delta V$th, the output voltage of the comparator 431 is at the "High" level, the output voltage of the inverter 433 is at the "Low" level, and the transistor 436 is maintained in an off state. During this period, the absolute value |VS| of the output voltage of the integration circuit 435 increases over time as shown in FIG. 14. While the output |VS| of the integration circuit 435 increases, the output $\Delta$|VS| of the differentiation circuit 437 assumes a constant value proportional to the rate of change of |VS|. Since the rate of change is a constant positive value, the value of $\Delta$|VS| is a constant positive value.

When the voltage $\Delta V$ subsequently decreases to a value lower than the voltage threshold $\Delta V$th, the transistor 436 is again turned off and the absolute value |VS| of the output voltage of the integration circuit 435 decreases to zero and the output $\Delta$|VS| of differential circuit 437 becomes a constant negative value which is proportional to the rate of change of |VS|. When $\Delta$|VS| falls below a preset value corresponding to the threshold voltage $\Delta$|VSth| (equal to the output of reference voltage source 439), the output of comparator 438 is switched to the "High" level.

Next, a measurement process for the frequency of breaths and the moisture content executed by the computation unit 34 according to this variation will be described with reference to FIG. 15. First, the computation unit 34 sets the counting value TC of the breath counter to "0" (Step S201). Next, the computation unit 434 determines whether the absolute value |VS| of an output voltage of the integration circuit 345 has fallen below the threshold level $\Delta V$th (Step S202). More particularly, it determines whether the voltage of the falling detector terminal teS has been switched from the "Low" level to the "High" level. The voltage of the falling detector terminal teS is maintained at the "Low" level while the output voltage $\Delta$|VS| of the differentiation circuit 437 is larger than the preset voltage threshold $\Delta$|VSth| and set to the "High" level when the output voltage $\Delta$|VS| becomes less than or equal to the voltage threshold $\Delta$|VSth|. If the computation unit 434 does not detect the falling of the absolute value |VS| of the output voltage of the integration circuit 345 to a level below $\Delta V$th (Step S202: No), an operation in Step S205 is directly executed. On the other hand, if falling of the absolute value |VS| of the output voltage of the integration circuit 345 to a level below $\Delta V$th has been detected (Step S202: Yes), the computation unit 34 increments the counting value TC by "1" (Step S203).

Next, the computation unit 34 refers the look-up table 342 recorded in the supplemental storage unit 34c, calculates a moisture content based on the output voltage VS of the integration circuit 345 when the absolute value |VS| has fallen to a level below $\Delta V$th and records the calculated moisture content in the supplemental storage unit 34c (Step S204). Here, the computation unit 34 first calculates a proportional value proportional to the time period extending from the last time the absolute value |VS| has fallen to a level below ΔVth until the most recent time the absolute value |VS| has fallen to a level below ΔVth. Next, the computation unit 34 takes a value obtained by dividing of the output voltage of the integration circuit 345 by the calculated proportional value as an average value of the output voltage ΔV of the detector circuit 2 and calculates the moisture content referring the look-up table.

Thereafter, the computation unit 34 determines whether or not the measuring period has ended (Step S205). If the measuring period has not ended (Step S205: No), the computation unit 34 again executes the operation in Step S202. On the other hand, if the measuring period has ended (Step S205: Yes), the computation unit 34 records the counting value TC of the breath counter as the frequency of breaths in the supplemental storage unit 34c (Step S206), and terminates the measurement process for the frequency of breaths and the moisture content.

According to this configuration, calculation of an integration value of the voltage ΔV output from the detector circuit 2 is performed using the integration circuit 435 and the differentiation circuit 437. With this, a number of operations to be executed by the computation unit 434 may be reduced and therefore it is possible to reduce loads on the computation unit 434.

In the foregoing embodiments, the calculation unit 3 calculates the moisture content using the look-up table 342. However, the present invention is not limited to such an example, and the calculation unit 3 may calculate the moisture content using a function expression expressing the correlation between a potential difference between the first electrode 12 and the second electrode 13 and the moisture content in the breath, for example. According to this configuration, the supplemental storage unit 34c is only required to record a shape of the function expression and an amount of information to be recorded in the supplemental storage unit 34c. Therefore, it is possible to reduce a capacity of the supplemental storage unit 34c.

While the embodiment and the variations of the present invention has been described above, the present invention is not limited to the above description. The present invention includes an appropriate combination of the embodiment and the variations, as well as modification to such a combination as appropriate.

The present application is based on Japanese Patent Application No. 2015-83283 filed on Apr. 15, 2015. The specification, the scope of the invention, and the drawings of Japanese Patent Application No. 2015-83283 in their entirety are incorporated herein by reference.

DESCRIPTION OF REFERENCE SYMBOLS 1, 201, 501: breath sensor
2: detector circuit
3, 303: calculation unit
4: display unit
11, 211: base body
12, 212: first electrode
13, 213: second electrode
14, 214: covering layer
16a, 16b: lead wire
21: differential amplifier
33: ADC
34, 334, 434: computation unit
34a: CPU
34b: main storage unit
34c: supplemental storage unit
34d: input unit
34e: output unit
34f: interface unit
34g: system bus
331, 431, 438: comparator
332, 432, 439: reference voltage source
333: AND circuit
342: look-up table
432, 439: reference voltage sources
433: inverter
435: integration circuit
435a, 437a: operational amplifier
436: transistor
437: differentiation circuit
C1, C2: capacitor
R1, R2: resistor

The invention claimed is:

1. A breath sensor comprising: a base body having an outer surface;
   a first electrode provided on a first part of the outer surface of the base body;
   a second electrode provided on a second part of the outer surface of the base body; and
   a covering layer made of a material that does not pass moisture there through, the covering layer covering the second electrode,
   the base body being made of a material whose surface potential changes due to attachment of moisture to the surface of the first electrode and or the outer surface of the base body.

2. The breath sensor according to claim 1, wherein
   the base body includes first and second opposed surfaces;
   the first electrode is provided on the first surface of the base body; and
   the second electrode is provided on the second surface of the base body.

3. The breath sensor according to claim 1, wherein:
   the base body includes a main surface; and
   the first and second electrodes are provided on the main surface of the base body.

4. The breath sensor according to claim 3, wherein the main surface is planar.

5. The breath sensor according to claim 1, wherein the covering layer comprises a cation exchange membrane.

6. The breath sensor according to claim 1, wherein the base body comprises an anion exchange member.

7. The breath sensor according to claim 6, wherein the base body further comprises a cation exchange member.

8. The breath sensor according to claim 7, wherein the cation and anion exchange members are both planar membranes and lie one on top of the other with the anion exchange member being adjacent the first electrode and the cation exchange member being adjacent the second electrode.

9. The breath sensor according to claim 1, wherein the outer surface of the base body include first and second surfaces and the first and second electrodes are located on the first and second surfaces, respectively.

10. The breath sensor according to claim 9, wherein the first and second electrodes cover the entirety of the first and second surfaces.

11. The breath sensor according to claim 1, wherein the outer surface of the base body includes a planar first surface and first and second electrodes are located on the first surface.

12. The breath sensor according to claim 1, wherein the base body is made of an ion exchange material.

13. A breath sensor unit comprising:
the breath sensor according to claim 1;
a detector circuit configured to detect a potential difference between the first and second electrodes; and
a breath frequency calculation unit configured to calculate the number of breaths applied to the breath sensor during a predetermined period of time based on fluctuations of the potential difference.

14. The breath sensor unit according to claim 13, further comprising:
a memory for recording correlated information indicating a correlation between the potential difference and a moisture content; and
a moisture content calculation unit configured to calculate the moisture content in a breath based on the stored correlated information and the potential difference detected by the detector circuit.

15. A breath sensing method, comprising:
(a) detecting a potential difference between a first electrode and a second electrode of a breath sensor of the type that includes:
(1) a base body;
(2) the first and second electrodes being located on the base body; and
(3) a covering layer covering the second electrode and made of a material that does not pass moisture there through, the base body being made of a material whose surface potential changes due to attachment of moisture to a surface of the first electrode and/or a surface of the base body; and
calculating a number of breaths within a predetermined period of time based on fluctuation of the potential difference.

16. The breath sensing method according to claim 15, further comprising:
calculating a moisture content in a single breath based on stored correlated information indicating a correlation between the potential difference during the single breath and the moisture content in the single breath.

17. The breath sensing method according to claim 15, wherein the base body is made of an ion exchange material.

* * * * *